United States Patent [19]

Krämer et al.

[11] 4,284,639
[45] Aug. 18, 1981

[54] COMBATING FUNGI WITH 1-PHENOXY-2-(2,4-DICHLOROPHENYL)-1-(1,2,4-TRIAZOL-1-YL)-ETHAN-2-ONES AND -OLS

[75] Inventors: Wolfgang Krämer; Karl H. Büchel, both of Wuppertal; Wilhelm Brandes, Leichlingen; Paul-Ernst Frohberger, Leverkusen; Manfred Plempel, Wuppertal, all of Fed. Rep. of Germany

[73] Assignee: Bayer Aktiengesellschaft, Leverkusen, Fed. Rep. of Germany

[21] Appl. No.: 125,724

[22] Filed: Feb. 28, 1980

Related U.S. Application Data

[63] Continuation of Ser. No. 28,620, Apr. 9, 1979, abandoned, which is a continuation of Ser. No. 872,988, Jan. 27, 1978, abandoned.

[30] Foreign Application Priority Data

Feb. 11, 1977 [DE] Fed. Rep. of Germany ....... 2705678
Feb. 11, 1977 [DE] Fed. Rep. of Germany ....... 2705679

[51] Int. Cl.$^3$ .................. A01N 43/64; C07D 249/08; A61K 31/41
[52] U.S. Cl. .................................. 424/269; 548/262; 568/331
[58] Field of Search .................. 548/262; 424/269

[56] References Cited

U.S. PATENT DOCUMENTS

| | | | |
|---|---|---|---|
| 3,912,752 | 10/1975 | Meiser et al. | 548/262 |
| 3,952,002 | 4/1976 | Kramer et al. | 548/262 |
| 4,013,677 | 3/1977 | Stolzer et al. | 548/262 |
| 4,036,967 | 7/1977 | Meiser et al. | 548/262 |

FOREIGN PATENT DOCUMENTS

| | | | |
|---|---|---|---|
| 2247186 | 3/1974 | Fed. Rep. of Germany | 548/262 |
| 2324424 | 12/1974 | Fed. Rep. of Germany | 548/262 |

*Primary Examiner*—Alton D. Rollins
*Attorney, Agent, or Firm*—Sprung, Felfe, Horn, Lynch & Kramer

[57] ABSTRACT

1-Phenoxy-2-(2,4-dichlorophenyl)-1-(1,2,4-triazol-1-yl)-ethan-2-ones and -ols of the formula

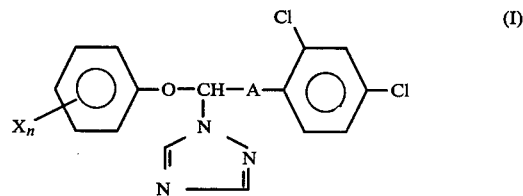

in which
A is —C(O)— or —CH(OH)—,
X each independently is halogen, alkyl or optionally substituted phenyl, and
n is 0, 1, 2 or 3, or a salt thereof, which possess fungicidal and antimicrobial properties rendering them useful in agriculture and pharmacy.

11 Claims, No Drawings

COMBATING FUNGI WITH 1-PHENOXY-2-(2,4-DICHLOROPHENYL)-1-(1,2,4-TRIAZOL-1-YL)-ETHAN-2-ONES AND -OLS

This is a continuation of application Ser. No. 028,620, filed Apr. 9, 1979, now abandoned, which in turn became a continuation of parent Ser. No. 872,988 filed Jan. 27, 1978, now abandoned.

The present invention relates to and has for its objects the provision of particular new 1-phenoxy-2-(2,4-dichlorophenyl)-1-(1,2,4-triazol-1-yl)-ethan-2-ones and -ols which possess fungicidal and antimicrobial properties, active compositions in the form of mixtures of such compounds with solid and liquid dispersible carrier vehicles, and methods for producing such compounds and for using such compounds in a new way especially for combating pests, e.g. fungi and microbes, with other and further objects becoming apparent from a study of the within specification and accompanying examples.

It has already been disclosed in U.S. Pat. Nos. 3,912,752 and 3,952,002 that certain 3,3-dimethyl-1-phenoxy-1-triazolylbutan-2-ones and -ols possess fungicidal activity. However, their action is not always completely satisfactory, in particular when low application amounts and concentrations are used.

It has also been disclosed in German Published Specifications DOS 2,247,186 and 2,324,424 that phenoxy-triazolyl derivatives have a good antimycotic action. However, their action, in particular against dermatophytes, is not always completely satisfactory.

The present invention provides, as new compounds, the 2,4-dichlorophenyl-triazolyl-ethan-ones and -ols of the general formula

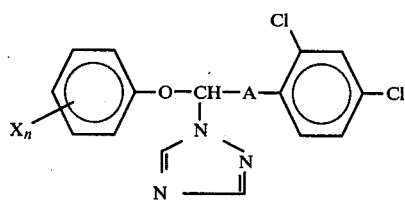

in which
A represents a keto group or a CH(OH) grouping,
X represents halogen, alkyl or optionally substituted phenyl and
n represents 0,1,2 or 3, the X substituents being selected independently of one another when n is 2 or 3,
and their salts.

The compounds of this invention have powerful fungicidal and antimicrobial, especially antimycotic, properties.

Preferably, X represents fluorine, chlorine, bromine, iodine, straight-chain or branched alkyl with 1 to 4 carbon atoms or phenyl which is optionally substituted by halogen (especially chlorine) and n represents 0, 1 or 2.

Those compounds of the formula (I) in which A represents the CH(OH) group possess two asymmetric carbon atoms; they can therefore be present in the form of both geometric isomers (erythro form and threo form), which can be obtained in different proportions. In both cases, they are present as optical isomers. The formula (I) is intended to include all the isomers.

Surprisingly, the active compounds according to the invention exhibit a considerably higher fungicidal activity, in particular against cereal diseases, and higher antimycotic activity than the 3,3-dimethyl-1-phenoxy-1-triazolyl-butan-2-ones and -ols which are known from the state of the art and which are related compounds chemically and from the point of view of their activity. The active compounds according to the invention are thus an enrichment of the art.

The invention also provides a process for the preparation of a 3,4-dichlorophenyl-triazolyl-ethan-one or -ol of the formula (I), in which a 1-bromo-2-(2,4-dichlorophenyl)-1-phenoxy-ethan-2-one of the formula

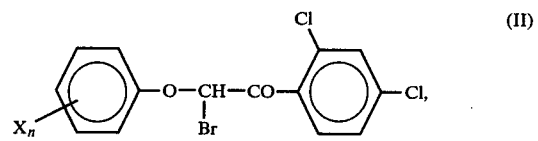

in which X and n have the meanings stated above,
is reacted with 1,2,4-triazole in the presence of a diluent and of an acid binding agent, and, if required, the 1,2,4-triazolylethanone thereby obtained is reduced with a complex borohydride in a manner which is in itself known, optionally in the presence of a diluent.

Furthermore, the 2,4-dichlorophenyl-triazolyl-ethan-ones and -ols obtainable according to the invention can be converted into salts thereof (preferably the physiologically acceptable salts) by reaction with acids.

If 1-bromo-1-(4-chlorophenoxy)-2-(2,4-dichlorophenyl)-ethan-2-one and 1,2,4-triazole are used as starting materials, the course of the reaction can be represented by the following equation:

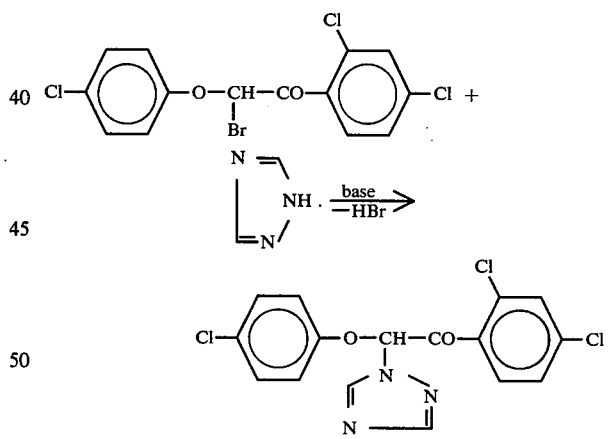

If 1-(4-chlorophenoxy)-2-(2,4-dichlorophenyl)-1-(1,2,4-triazol-1-yl)-ethan-2-one is reduced with sodium borohydride the course of the reaction can be represented by the following equation:

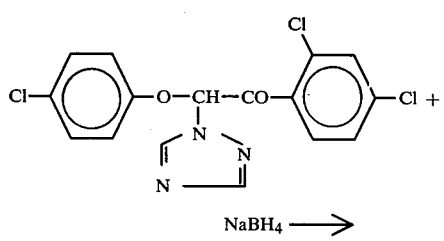

NaBH$_4$ ⟶

-continued

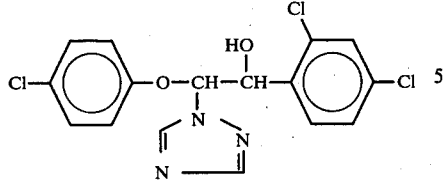

Examples which may be mentioned of starting materials of the formula (II) are: 1-bromo-1-phenoxy-2-(2,4-dichlorophenyl)-ethan-2-one, 1-bromo-1-(4-chlorophenoxy)-2-(2,4-dichlorophenyl)-ethan-2-one, 1-bromo-1-(4-fluorophenoxy)-2-(2,4-dichlorophenyl)-ethan-2-one, 1-bromo-1-(4-bromophenoxy)-2-(2,4-dichlorophenyl)-ethan-2-one, 1-bromo-1-(4-iodophenoxy)-2-(2,4-dichlorophenyl)-ethan-2-one, 1-bromo-1-(2,4-dichlorophenoxy)-2-(2,4-dichlorophenyl)-ethan-2-one, 1-bromo-1-(2,6-dichlorophenoxy)-2-(2,4-dichlorophenyl)-ethan-2-one, 1-bromo-1-(2,5-dichlorophenoxy)-2-(2,4-dichlorophenyl)-ethan-2-one, 1-bromo-1-(3-fluorophenoxy)-2-(2,4-dichlorophenyl)-ethan-2-one, 1-bromo-1-(3-chlorophenoxy)-2-(2,4-dichlorophenyl)-ethan-2-one, 1-bromo-1-(3-bromophenoxy)-2-(2,4-dichlorophenyl)-ethan-2-one, 1-bromo-1-(2-chlorophenoxy)-2-(2,4-dichlorophenyl)-ethan-2-one, 1-bromo-1-(4-methylphenoxy)-2-(2,4-dichlorophenyl)-ethan-2-one, 1-bromo-1-(4-ethylphenoxy)-2-(2,4-dichlorophenyl)-ethan-2-one, 1-bromo-1-(3-methylphenoxy)-2-(2,4-dichlorophenyl)-ethan-2-one, 1-bromo-1-(2-methylphenoxy)-2-(2,4-dichlorophenyl)-ethan-2-one, 1-bromo-1-(2-isopropylphenoxy)-2-(2,4-dichlorophenyl)-ethan-2-one, 1-bromo-1-(4-chloro-2-methylphenoxy)-2-(2,4-dichlorophenyl)-ethan-2-one, 1-bromo-1-(4-bromo-2-methylphenoxy)-2-(2,4-dichlorophenyl)-ethan-2-one, 1-bromo-1-(4-fluoro-2-methylphenoxy)-2-(2,4-dichlorophenyl)-ethan-2-one, 1-bromo-1-(4-iodo-2-methylphenoxy)-2-(2,4-dichlorophenyl)-ethan-2-one, 1-bromo-1-(2,3-dimethylphenoxy)-2-(2,4-dichlorophenyl)-ethan-2-one, 1-bromo-1-(4-biphenylyloxy)-2-(2,4-dichlorophenyl)-ethan-2-one, 1-bromo-1-(4-4'-chlorobiphenylyloxy)-2-(2,4-dichlorophenyl)-ethan-2-one, 1-bromo-1-(4-2',4'-dichlorobiphenylyloxy)-2-(2,4-dichlorophenyl)-ethan-2-one, 1-bromo-1-(4-2,4'-dichlorophenylyloxy)-2-(2,4-dichlorophenyl)-ethan-2-one, 1-bromo-1-(4,4'-bromobiphenylyloxy)-2-(2,4-dichlorophenyl)-ethan-2-one and 1-bromo-1-(4-2-chlorobiphenylyloxy)-2-(2,4-dichlorophenyl)-ethan-2-one.

The 1-bromo-2-(2,4-dichlorophenyl)-1-phenoxyethan-2-ones of the formula (II) to be used as starting materials have not yet been described in the literature, but can be prepared by known processes, by reacting known phenols of the general formula

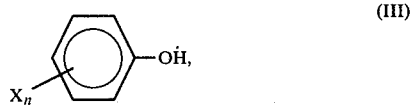

in which X and n have the meanings stated above, with the bromoacetophenone of the formula

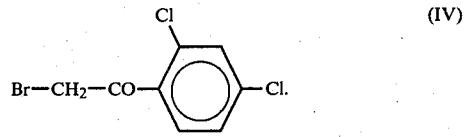

The active hydrogen atom which still remains is then replaced by bromine in the customary manner.

Preferred salts of the compounds of the formula (I) are—for reasons of phytotoxicity—salts with physiologically acceptable acids. The preferred acids include the hydrogen halide acids (for example hydrobromic acid and, in particular, hydrochloric acid), phosphoric acid, nitric acid, monofunctional and bifunctional carboxylic acids and hydroxycarboxylic acids (for example acetic acid, citric acid, sorbic acid and lactic acid), and 1,5-naphthalenedisulphonic acid.

Preferred diluents for the reaction according to the invention are inert organic solvents, especially ketones, such as diethyl ketone and, in particular, acetone and methyl ethyl ketone; nitriles, such as propionitrile and, in particular, acetonitrile, alcohols, such as ethanol or isopropanol; ethers, such as tetrahydrofuran or dioxane; aromatic hydrocarbons, such as toluene, 1,3-dichlorobenzene and benzene; formamides, such as, in particular, dimethylformamide; and halogenated hydrocarbons, such as methylene chloride, carbon tetrachloride or chloroform.

The reaction is carried out in the presence of an acid-binding agent. It is possible to add any of the inorganic or organic acid-binding agents which can be customarily used, such as alkali metal carbonates, for example sodium carbonate, potassium carbonate and sodium bicarbonate, or such as lower tertiary alkylamines, cycloalkylamines or aralkylamines, for example triethylamine, N,N-dimethylcyclohexylamine, dicyclohexylmethylamine and N,N-dimethylbenzylamine, and furthermore pyridine and diazabicyclooctane. Preferably, an appropriate excess of the 1,2,4-triazole is used.

The reaction temperatures can be varied within a relatively wide range. In general, the reaction is carried out at from 0° to 150° C., preferably at from 60° to 120° C., in the presence of a solvent, such as acetone or methyl ethyl ketone.

In carrying out the process according to the invention, 1 to 2 moles of 1,2,4-triazole and 1 to 2 moles of acid-binding agent are preferably employed per mole of the compound of the formula (II). In order to isolate the compound of the formula (I), the solvent is distilled off, the residue is taken up in an organic solvent and the organic solution is washed with water. The organic phase is dried over sodium sulphate and freed from solvent in vacuo. The residue is purified by distillation or recrystallization.

For the reduction according to the invention, suitable diluents are polar organic solvents, especially alcohols, such as methanol, ethanol, butanol and isopropanol, and ethers, such as diethyl ether or tetrahydrofuran. In general, the reduction reaction is carried out at from 0° to 30° C., preferably at from 0° to 20° C. For this reaction, about 1 mole of a borohydride, such as sodium borohydride or lithium borohydride, is preferably employed per mole of the compound of the formula (II). In order to isolate the compound of the formula (I), the residue is taken up, for example, in dilute hydrochloric acid and the acid solution is then rendered alkaline and extracted with an organic solvent, or only water is added and the product is extracted by shaking with an organic solvent. Further working up is carried out in the customary manner.

Examples which may be mentioned of particularly active representatives of the active compounds according to the invention are the following: 1-(2-chlorophenoxy)-2-(2,4-dichlorophenyl)-1-(1,2,4-triazol-1-yl)-ethan-2-one or -ol, 1-(2-isopropylphenoxy)-2-(2,4-dichlorophenyl)-1-(1,2,4-triazol-1-yl)-ethan-2-one or -ol, 1-(2-methylphenoxy)-2-(2,4-dichlorophenyl)-1-(1,2,4-triazol-1-yl)-ethan-2-one or -ol, 1-(2-chloro-4-methylphenoxy)-2-(2,4-dichlorophenyl)-1-(1,2,4-triazol-1-yl)-ethan-2-one or -ol, 1-(4-bromophenoxy)-2-(2,4-dichlorophenyl)-1-(1,2,4-triazol-1-yl)-ethan-2-one and -ol, 1-(4-iodophenoxy)-2-(2,4-dichlorophenyl)-1-(1,2,4-triazol-1-yl)-ethan-2-one and -ol, 1-(2,6-dichlorophenoxy)-2-(2,4-dichlorophenyl)-1-(1,2,4-triazol-1-yl)-ethan-2-one and -ol, 1-(2,5-dichlorophenoxy)-2-(2,4-dichlorophenyl)-1-(1,2,4-triazol-1-yl)-ethan-2-one and -ol, 1,(3-fluorophenoxy)-2-(2,4-dichlorophenyl)-1-(1,2,4-triazol-1-yl)-ethan-2-one and -ol, 1-(3-bromophenoxy)-2-(2,4-dich-1,(3-fluorophenoxy)-2-(2,4-dichlorophenyl)-1-(1,2,4-triazol-1-yl)-ethan-2-one and -ol, 1-(3-bromophenoxy)-2-(2,4-dichlorophenyl)-1-(1,2,4-triazol-1-yl)-ethan-2one and -ol, 1-(4-methylphenoxy)-2-(2,4-dichlorophenyl)-1-(1,2,4-triazol-1-yl)-ethan-2-one and -ol, 1-(4-ethylphenoxy)-2-(2,4-dichlorophenyl)-1-(1,2,4-triazol-1-yl)-ethan-2-one and -ol, 1-(3-methylphenoxy)-2-(2,4-dichlorophenyl)-1-(1,2,4-triazol-1-yl)-ethan-2-one and -ol, 1-(2-methylphenoxy)-2-(2,4-dichlorophenyl)-1-(1,2,4-triazol-1-yl)-ethan-2-one and -ol, 1-(4-chloro-2-methylphenoxy)-2-(2,4-dichlorophenyl)-1-(1,2,4-triazol-1-yl)-ethan-2-one and -ol, 1-(4-bromo-2-methylphenoxy)-2-(2,4-dichlorophenyl)-1-(1,2,4-triazol-1-yl)-ethan-2-one and -ol, 1-(4-fluoro-2-methylphenoxy)-2-(2,4-dichlorophenyl)-1-(1,2,4-triazol-1-yl)-ethan-2-one and -ol, 1-(4-iodo-2-methylphenoxy)-2-(2,4-dichlorophenyl)-1-(1,2,4-triazol-1-yl)-ethan-2-one and -ol, 1-(2,3-dimethylphenoxy)-2-(2,4-dichlorophenyl)-1-(1,2,4-triazol-1-yl)-ethan-2-one and -ol, 1-(4-2',4'-dichlorobiphenylyloxy)-2-(2,4-dichlorphenyl)-1-(1,2,4-triazol-1-yl)-ethan-2-one and -ol, 1-(4-2,4'-dichlorobiphenylyloxy)-2-(2,4-dichlorophenyl)-1-(1,2,4-triazol-1-yl)-ethan-2-one and -ol, 1-(4-4'-bromobiphenylyloxy)-2-(2,4-dichlorophenyl)-1-(1,2,4-triazol-1-yl)-ethan-2-one and -ol and 1-(4-2-chlorobiphenylyloxy)-2-(2,4-dichlorophenyl)-1-(1,2,4-triazol-1-yl)-ethan-2-one and -ol.

Other examples are mentioned in the preparative examples given later in this specification.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens.

They display a particularly good activity against parasitic fungi on above-ground parts of plants.

As plant protection agents, the active compounds according to the invention can be used with particularly good success for combating powdery mildew fungi, for example for combating powdery mildew of cucumber (*Erysiphe cichoriacearum*), powdery mildew of apples (*Podosphaera leucotricha*) and powdery mildew of cereals, as well as other cereal diseases, for example cereal rust.

As plant protection agents, the active compounds according to the invention can be used for the treatment of seed or soil and for the treatment of above-ground parts of plants.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanoloamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alum and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for the purpose: emulsifying agents, such as non-ionic and/or anionic emulsifying agents (e.g. polyethylene oxide esters of fatty acids polyethylene oxide ethers of fatty alcohols, alkyl sulfates, alkyl sulfonates, aryl sulfonates, albumin hydrolyzates, etc. and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, arthropodicides, nematicides, bactericides, rodenticides, herbicides, fertilizers, growth-regulating agents, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10% by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Especially when used as leaf fungicides, the active compound concentrations in the use forms can be varied within a fairly wide range. They are, in general, from 0.01 to 0.00001 percent by weight, preferably from 0.05 to 0.0001 percent.

For treatment of seed, amounts of active compound of from 0.001 to 50 g per kilogram of seed, preferably from 0.01 to 10 g, are generally employed.

For the treatment of soil, amounts of from 1 g to 1000 g per cubic meter of soil, preferably of from 10 to 200 g, are generally employed.

Furthermore, the present invention contemplates method of selectively killing, combating or controlling pests, e.g. fungi which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The compounds of the formula (I), which can be used according to the invention, and their salts, exhibit antimicrobial, in particular powerful antimycotic, effects. They possess a very broad spectrum of antimycotic activity, especially against dermatophytes and blastomyces as well as biphase fungi, for example against varieties of Candida, such as Candida albicans, varieties of Epidermophyton, such Epidermophyton floccosum, varieties of Aspergillus, such as Aspergillus niger and Aspergillus fumigatus, varieties of Trichophyton, such as Trichophyton mentagrophytes, varieties of Microsporon, such as Microsporon felineum and varieties of Penicillium, such as Penicillium commune. The recital of these micro-organisms in no way implies a limitation of the germs which can be combated but is only of illustrative character.

The following may be mentioned as examples of fields of indication in human medicine: dermatomycoses and systemic mycoses caused by Trichophyton mentagrophytes and other varieties of Trichophyton, varieties of Microsporon, Epidermophyton floccosum, blastomyces and biphase fungi as well as moulds.

The following may be mentioned as examples of fields of indication in veterinary medicine: generally all dermatomycoses and systemic mycoses, especially those caused by the above mentioned pathogens.

As stated above, the invention also relates to the use in human and veterinary medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain coloring agents and preservatives as well as perfumes and flavoring additions (e.g. peppermint oil and eucalyptus oil) and sweetening agents (e.g. saccharin).

The pharmaceutical compositions according to the invention generally contain from 0.1 to 99.5 usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of these mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is from 0.5 to 15 g preferably from 2.5 to 10 g of active ingredient.

The production of the above mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, or intravenously), rectally or locally, preferably parenterally, especially intravenously. Preferred pharmaceutical compositions and medicaments are therefore those adapted for intravenous administration, such as sterile and blood-isotonic solutions and emulsions and ampoules containing them. Administration in the method of the invention is preferably intravenously.

In general it has proved advantageous to administer amounts of from 10 mg to 300 mg/kg of body weight most preferably from 50 to 200 mg/kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above mentioned minimum dosage rate, whilst other cases the upper limit mentioned must be exceeded to achieve the desired results. Where larger amounts are administered it can be advisable to divide these into several individual administrations over the course of the day.

The preparation of the new compounds of the present invention is illustrated, without limitation, by the following examples:

EXAMPLE 1

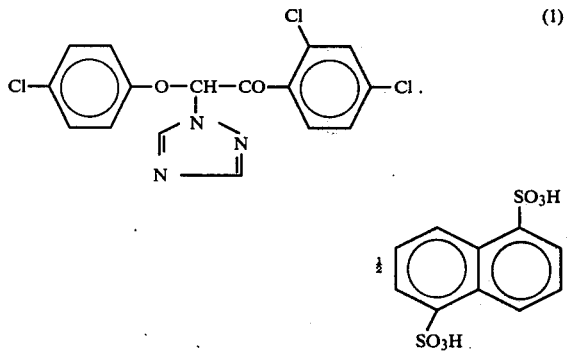

244.6 g (0.62 mol) of 1-bromo-1-(4-chlorophenoxy)-2-(2,4-dichlorophenyl)-ethan-2-one were added dropwise, at the boil, to 149 g (2.13 mol) of 1,2,4-triazole in 1,500 ml of acetonitrile. The mixture was heated under reflux for 40 hours. Thereafter, the solvent was distilled off in vacuo, the residue was taken up in 1,000 ml of methylene chloride and the methylene chloride solution was extracted by shaking three times each with 500 ml of water. The aqueous phase was again extracted by shaking with 500 ml of methylene chloride. The combined methylene chloride phases were dried over sodium sulphate and concentrated by distilling off the solvent in vacuo. The residue was dissolved in 300 ml of acetone and 100 g of 1,5-naphthalenedisulphonic acid hexahydrate in 200 ml of acetone were added. This gave 270 g (41.3% of theory) of 1-(4-chlorophenoxy)-2-(2,4-dichlorophenyl)-1-(1,2,4-triazol-1-yl)-ethan-2-one naphthalene-1,5-disulphonate of melting point 198° C.

EXAMPLE 2

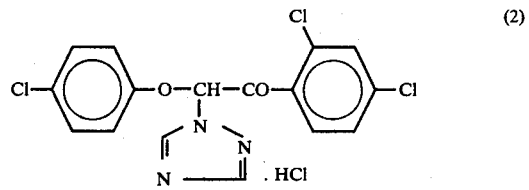

The base was liberated from the 1-(4-chlorophenoxy)-2-(2,4-dichlorophenyl)-1-(1,2,4-triazol-1-yl)-ethan-2-one naphthalene-1,5-disulphonate, obtained according to Example 1, by adding sodium bicarbonate solution, and was taken up in ethyl acetate and converted, with ethereal hydrochloric acid, into the hydrochloride, which crystallized out after standing for a long time in ether. 1-(4-Chlorophenoxy)-2-(2,4-dichlorophenyl)-1-(1,2,4-triazol-1-yl)-ethan-2-one hydrochloride of melting point 138°-140° C. was quantitatively obtained.

Preparation of the starting products

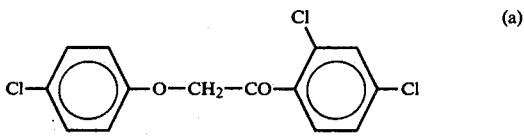

256 g (2 moles) of 4-chlorophenol were dissolved in 2 l of toluene and 280 g of potash (potassium carbonate) were added. The suspension was heated for 2 hours at a water separator, during which 200 ml of toluene distil off. Thereafter, 450 g (2 moles) of ω-chloro-2,4-dichloroacetophenone in 400 ml of toluene were added dropwise during refluxing, and the mixture was heated at a water separator for additional 12 hours. After cooling down, the solution was washed once with 2 l of water, once with 1000 ml of a 10 percent solution of sodium hydroxide, and thereafter once with 2 l of water, and the toluene-phase was dried over sodium sulphate, and the solvent distilled off in vacuo of a waterjet pump. The crystalline residue was stirred up with 800 ml of ligroine, filtered with suction and dried. 448 g (71% of theory) of ω-(4-chlorophenoxy)-2,4-dichloroacetophenone of melting point 93°-95° C. were obtained.

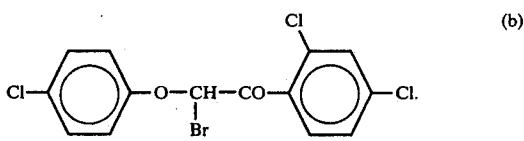

448 g (1.43 moles) of ω-(4-chlorophenoxy)-2,4-dichloroacetophenone were dissolved in 3 l of chloroform, 5 ml of ether saturated with hydrogen chloride were added and 75 ml of bromine were added dropwise in such a way that continuous decolorization could be observed. The mixture was stirred after the addition for 1 hour at 40° C. and the chloroform distilled off in vacuo of a water-jet pump. 572 g of raw 1-bromo-1-(4-chlorophenoxy)-2-(2,4-dichlorophenyl)-ethan-2-one were obtained, which might be used immediately for the reaction described in Example 1 above.

EXAMPLE 3

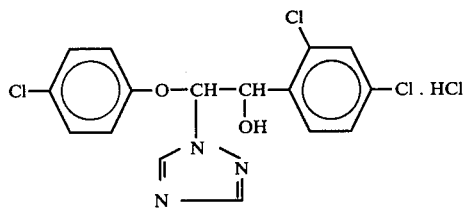 (3)

226 g (0.42 mol) of 1-(4-chlorophenoxy)-2-(2,4-dichlorophenyl)-1-(1,2,4-triazol-1-yl)-ethan-2-one naphthalene-1,5-disulphonate (Example 1) were suspended in 500 ml of methylene chloride, 1,000 ml of saturated sodium bicarbonate solution were added and the mixture was stirred for 5 hours. The isolated organic phase was dried over sodium sulphate and concentrated in vacuo. The residue was taken up in 1.5 liters of methanol, 17 g (0.45 mol) of sodium borohydride were added in portions of about 1 g at 0° to 5° C. and the mixture was stirred for 15 hours at room temperature. 200 ml of concentrated hydrochloric acid were then added dropwise at 0° C. and the mixture was again stirred for 15 hours at room temperature. The reaction mixture was then stirred into 1,000 ml of saturated sodium bicarbonate solution, the aqueous phase was extracted by shaking twice each with 500 ml of methylene chloride and the organic phase was extracted by shaking twice each with 200 ml of water. The combined organic phases were dried over sodium sulphate and concentrated by distilling off the solvent in vacuo. The oil which remained was dissolved in 800 ml of ether and dry hydrogen chloride was added in excess. This gave 113.5 g (64% of theory) of 1-(4-chlorophenoxy)-2-(2,4-dichlorophenyl)-1-(1,2,4-triazol-1-yl)-ethan-2-ol hydrochloride as an isomer mixture of melting point 157°–172° C.

The compounds which are disclosed in Table 1, which follows, were obtained analogously to the above-mentioned examples.

TABLE 1

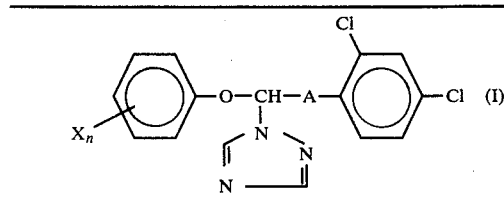 (I)

| Compound No. | $X_n$ | A | Melting point (°C.) | |
|---|---|---|---|---|
| 4 | 2,4-Cl$_2$ | CO | 173–83 | (.HCl) |
| 5 | 4-C$_6$H$_5$ | CO | 205–08 | (.HCl) |
| 6 | 4-(C$_6$H$_4$)-Cl | CO | 136 | (decomposition) (.HCl) |
| 7 | 4-F | CO | 83–86 | |
| 8 | 2,6-Cl$_2$ | CO | 176 | (.HCl) |
| 9 | 3-Cl | CO | 140–42 | (.HCl) |
| 10 | — | CO | 86–88 | |

TABLE 1-continued

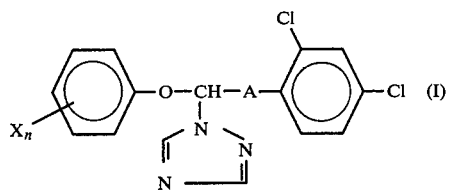 (I)

| Compound No. | $X_n$ | A | Melting point (°C.) | |
|---|---|---|---|---|
| 11 | 4-CH$_3$ | CO | 172 | (.HCl) |
| 12 | 4-Cl,2-CH$_3$ | CO | 138 | (.HCl) |
| 13 | 4-I | CO | 156 | (.HCl) |
| 14 | 2,4-Cl$_2$ | CH(OH) | 68–85 | (.HCl) isomer mixture |
| 15 | 4-C$_6$H$_5$ | CH(OH) | 148–150 | (.HCl) isomer mixture |
| 16 | 4-(C$_6$H$_4$)-Cl | CH(OH) | 170–74 | isomer mixture |
| 17 | 4-F | CH(OH) | 139–43 | (.HCl) isomer mixture |
| 18 | — | CH(OH) | 171–73 | isomer mixture |
| 19 | 3-Cl | CH(OH) | 155–58 | (.HCl) isomer mixture |

The activity of the compounds of this invention is illustrated by the following examples wherein the compounds according to the present invention are each identified by the number (given in brackets) from the preparative examples hereinabove.

The known comparison compounds are identified as follows:

(A) = 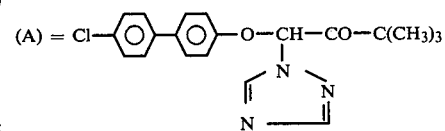

(B) = 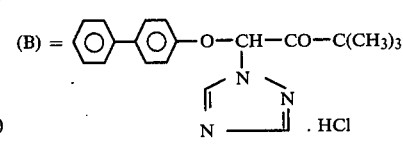

(C) = 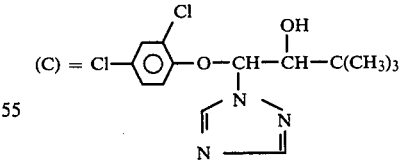

(D) = 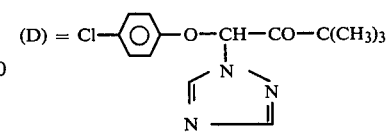

(E) = 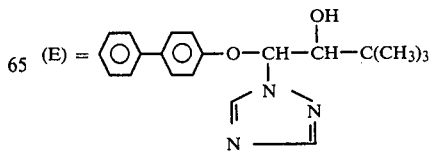

-continued

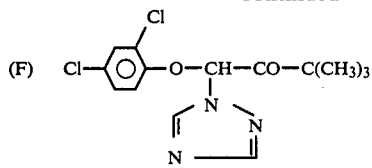

(F) (known)

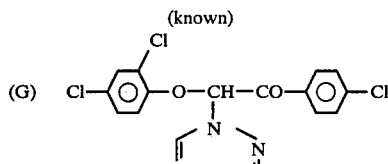

(G) (known)

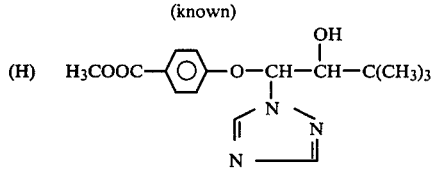

(H) (known)

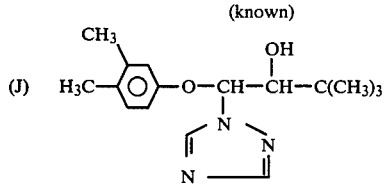

(J) (known)

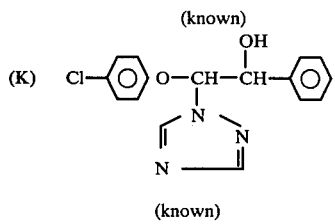

(K) (known)

EXAMPLE 4

Shoot treatment test/powdery mildew of cereal/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. hordei.

After 6 days' dwell time of the plants at a temperature of 21°–22° C. and 80–90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

The active compounds, active compound concentrations in the spray liquor and degrees of infection can be seen from the table which follows:

TABLE 2

| Shoot treatment test/powdery mildew of cereal/protective | | |
|---|---|---|
| Active compounds | Active compound concentration in the spray liquor in % by weight | Infection in % of the untreated control |
| untreated | — | 100 |
| (A) | 0.025 | 55.0 |
| (2) | 0.025 | 0.0 |
| (4) | 0.025 | 0.0 |
| (6) | 0.025 | 16.3 |
| (3) | 0.025 | 7.5 |
| (14) | 0.025 | 0.0 |
| (15) | 0.025 | 37.5 |
| (16) | 0.025 | 37.5 |

EXAMPLE 5

Shoot treatment test/cereal rust (leaf-destructive mycosis)/protective

To produce a suitable preparation of active compound, 0.25 part by weight of active compound was taken up in 25 parts by weight of dimethylformamide and 0.06 part by weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

After 10 days' dwell time of the plants at a temperature of 20° C. and 80–90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The more active the compound, the lower was the degree of rust infection.

The active compounds, active compound concentrations in the spray liquor and degrees of infection can be seen from the table which follows:

TABLE 3

| Shoot treatment test/cereal rust/protective | | |
|---|---|---|
| Active compounds | Active compound concentration in the spray liquor in % by weight | Infection in % of the untreated control |
| untreated | — | 100 |
| (B) | 0.025 | 33.8 |
| (C) | 0.025 | 33.8 |
| (2) | 0.025 | 12.5 |
| (5) | 0.025 | 10.0 |

EXAMPLE 6

Podosphaera test (apple)/protective
Solvent: 4.7 parts by weight of acetone

Emulsifier: 0.3 part by weight of alkylaryl polyglycol ether

Water: 95 parts by weight

The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated by dusting the conidia of the apple powdery mildew causative organism (*Podosphaera leucotricha*) and placed in a greenhouse at a temperature of 21°–23° C. and at a relative atmospheric humidity of about 70%.

10 days after the inoculation, the infection of the seedlings was determined. The assessment data were converted to % infection. 0% meant no infection; 100% meant that the plants were completely infected.

The active compounds, the concentrations of the active compounds and the results can be seen from the following table:

TABLE 4

Podosphaera test (apple)/protective

| Active compound | Infection in % at an active compound concentration of 0.001% |
|---|---|
| (D) | 42 |
| (2) | 25 |
| (3) | 0 |
| (14) | 0 |

EXAMPLE 7

Erysiphe test (cucumber)/protective

Solvent: 4.7 parts by weight of acetone

Emulsifier: 0.3 part by weight of alkylaryl polyglycol ether

Water: 95 parts by weight

The amount of the active compound required for the desired concentration of active compound in the spray liquid was mixed with the stated amount of solvent and the concentrate was diluted with the stated amount of water containing the stated amount of emulsifier.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cicohiacearum*. The plants were subsequently placed in a greenhouse at 23°–24° C. and at a relative atmospheric humidity of about 75%.

After 12 days, the infection of the cucumber plants was determined. The assessment data were converted to percent infection. 0% meant no infection; 100% meant that the plants were totally infected.

The active compounds, the concentrations of the active compounds and the results can be seen from the following table:

TABLE 5

Erysiphe test (cucumbers)/protective

| Active compound | Infection in % at an active compound concentration of 0.00025% |
|---|---|
| (E) | 62 |
| (2) | 12 |
| (3) | 6 |
| (14) | 16 |
| (15) | 12 |

EXAMPLE 8

Antimycotic in vitro activity

Description of the experiment

The in vitro tests were carried out in a series dilution test with germ inocula of an average of $5 \times 10^4$ germs/ml of substrate. The nutrient medium was (a) for dermatophytes and moulds: Sabouraud's milieu d'epreuve and (b) for yeasts; meat extract/glucose broth.

The incubation temperature was 28° C. and the duration of incubation was 24 to 96 hours.

The results of the tests of the activity of various compounds of the invention against diverse micro-organism are given in the following Table 6.

TABLE 6

Anti-mycotic in vitro activity

MINIMUM INHIBITORY CONCENTRATION VALUES in γ/ml of nutrient medium for

| Active compound (Compounds from Example No.) | Trichophyton mentagr. | Candida albicans | Penicillium commune | Aspergillus species | Microsporon felineum | Torulopsis glabrata |
|---|---|---|---|---|---|---|
| D | 4 | 40 | >100 | 100 | 100 | — |
| F | 4 | 40 | >100 | 100 | 100 | — |
| G | 4* | — | >100 | 100* | — | — |
| H | 4 | 64 | >64 | >64 | 64 | — |
| J | 4 | >64 | >64 | >64 | 64 | — |
| K | 64 | 64 | >64 | — | — | — |
| 2 | 4 | 32 | >64 | >64 | 32 | — |
| 3 | 4 | 8 | >64 | 64 | 32 | — |
| 5 | <1 | 32 | >64 | >64 | — | 32 |
| 14 | 4 | 8 | >64 | 64 | 32 | 32 |
| 15 | <1 | 32 | >64 | >64 | <1 | 1 |
| 16 | <1 | 8 | >64 | >64 | 4 | 1 |

* = 90% growth inhibition

It will be appreciated that the instant specification and examples are set forth by way of illustration and not limitation, and that various modifications and changes may be made without departing from the spirit and scope of the present invention.

What is claimed is:

1. A 1-phenoxy-1-(2,4-dichlorophenyl)-1-(1,2,4-triazol-1-yl)-ethan-2-one or -ol of the formula

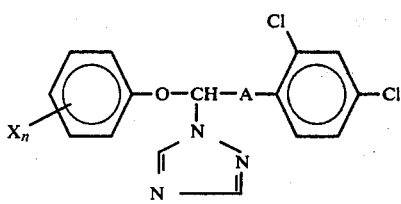

in which

A is —C(O)— or —CH(OH)—,

X each independently is halogen, alkyl with 1 to 4 carbon atoms, phenyl or halogen substituted phenyl, and n is 0, 1, 2 or 3, or a salt thereof.

2. A compound according to claim 1, in which

X is fluorine, chlorine, bromine, iodine, alkyl with 1 to 4 carbon atoms, phenyl or phenyl substituted by halogen, and n is 0, 1 or 2, or a salt thereof with a physiologically acceptable acid.

3. A compound according to claim 1, wherein such compound is 1-(4-chlorophenoxy)-2-(2,4-dichlorophenyl)-1-(1,2,4-triazol-1-yl)-ethan-2-one of the formula

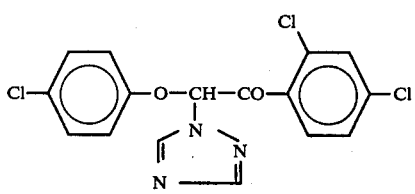

or a salt thereof.

4. A compound according to claim 1, wherein such compound is 1-(4-chlorophenoxy)-2-(2,4-dichlorophenyl)-1-(1,2,4-triazol-1-yl)-ethan-2-ol of the formula

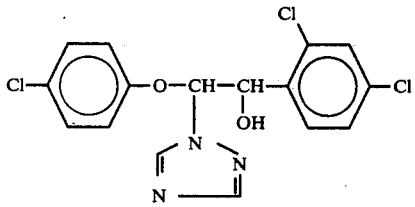

or a salt thereof.

5. A compound according to claim 1, wherein such compound is 1-(2,4-dichlorophenoxy)-2-(2,4-dichlorophenyl)-1-(1,2,4-triazol-1-yl)-ethan-2-one of the formula

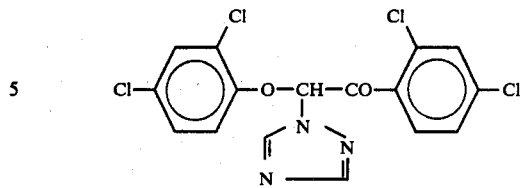

or a salt thereof.

6. A compound according to claim 1, wherein such compound is 1-(4-biphenylyloxy)-2-(2,4-dichlorophenyl)-1-(1,2,4-triazol-1-yl)-ethan-2-one of the formula

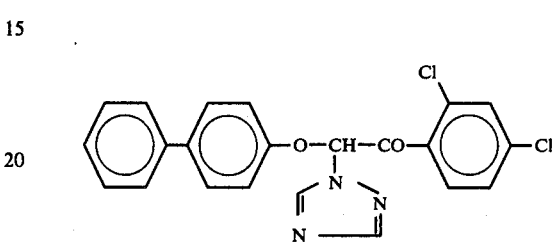

or a salt thereof.

7. A compound according to claim 1, wherein such compound is 1-(2,4-dichlorophenoxy)-2-(2,4-dichlorophenyl)-1-(1,2,4-triazol-1-yl)-ethan-2-ol of the formula

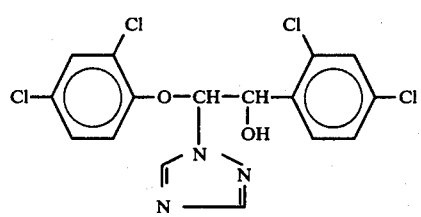

or a salt thereof.

8. A fungicidal or antimicrobial composition containing as active ingredient a fungicidally or antimicrobially effective amount of a compound or salt according to claim 1 in admixture with a diluent.

9. A method of combating fungi which comprises applying to the fungi, or to a habitat thereof, a fungicidally effective amount of a compound or salt according to claim 1.

10. A method according to claim 9, in which the compound is applied to plants, seed, or soil and is 1-(4-chlorophenoxy)-2-(2 4-dichlorophenyl)-1-(1,2,4-triazol-1-yl)-ethane-2-one, 1-(4-chlorophenoxy)-2-(2,4-dichlorophenyl)-1-(1,2,4-triazol-1-yl)-ethan-2-ol, 1-(2,4-dichlorophenoxy)-2-(2,4-dichlorophenyl)-1-(1,2,4-triazol-1-yl)-ethan-2-one, 1-(4-biphenylyloxy)-2-(2,4-dichlorophenyl)-1-(1,2,4-triazol-1-yl)-ethan-2-one or 1-(2,4-dichlorophenoxy)-2-(2,4-dichlorophenyl)-1-(1,2,4-triazol-1-yl)-ethan-2-ol, or a salt thereof.

11. A method of treating a patient suffering from microbial infection which comprises administering to such patient an antimicrobially effective amount of a compound or salt according to claim 1.

* * * * *